(12) United States Patent
Zhang et al.

(10) Patent No.: US 12,736,615 B2
(45) Date of Patent: Sep. 15, 2026

(54) RADAR SYSTEM HAVING A PHOTONICS-BASED SIGNAL GENERATOR

(71) Applicant: The University of Sydney, Sydney (AU)

(72) Inventors: Ziqian Zhang, Sydney (AU); Yang Liu, Sydney (AU); Benjamin John Eggleton, Sydney (AU)

(73) Assignee: The University of Sydney, Sydney (AU)

( * ) Notice: Subject to any disclaimer, the term of this patent is extended or adjusted under 35 U.S.C. 154(b) by 706 days.

(21) Appl. No.: 17/997,602

(22) PCT Filed: Apr. 30, 2021

(86) PCT No.: PCT/AU2021/050396
§ 371 (c)(1),
(2) Date: Oct. 31, 2022

(87) PCT Pub. No.: WO2021/217216
PCT Pub. Date: Nov. 4, 2021

(65) Prior Publication Data

US 2023/0236285 A1 Jul. 27, 2023

(30) Foreign Application Priority Data

May 1, 2020 (AU) ................................ 2020901389

(51) Int. Cl.
*G01S 7/03* (2006.01)
*A61B 5/0507* (2021.01)
(Continued)

(52) U.S. Cl.
CPC ............ *G01S 7/032* (2013.01); *A61B 5/0507* (2013.01); *G01S 7/352* (2013.01); *A61B 5/0816* (2013.01); *A61B 5/1126* (2013.01); *A61B 5/1135* (2013.01)

(58) Field of Classification Search
CPC ....... G01S 7/032; G01S 7/352; A61B 5/0507; A61B 5/0816; A61B 5/1126; A61B 5/1135
See application file for complete search history.

(56) References Cited

U.S. PATENT DOCUMENTS 8,750,717 B1 6/2014 Yap et al.
10,234,706 B2 3/2019 Guillet De Chatellus et al.
(Continued)

FOREIGN PATENT DOCUMENTS

CN 110212987 A 9/2019

OTHER PUBLICATIONS

Ma, Microwave Photonic Imaging Radar with a Millimeter-level Resolution, Apr. 9, 2020 (Year: 2020).*
(Continued)

*Primary Examiner* — Vladimir Magloire
(74) *Attorney, Agent, or Firm* — Lathrop GPM LLP; Tucker Griffith

(57) ABSTRACT

The present application relates to radio detection and ranging (radar) systems and, in particular, to a radar system having a photonics-based signal generator. Such a radar system comprises a stepped-frequency optical signal generator, an optical-to-electrical converter, and a transmitter. The stepped-frequency optical signal generator is configured for converting an optical signal into a stepped-frequency optical signal. The optical-to-electrical converter for converting the stepped-frequency optical signal into a stepped-frequency electrical signal. The transmitter for transmitting a microwave signal based on the stepped-frequency electrical signal.

18 Claims, 8 Drawing Sheets

(51) Int. Cl.

| | |
|---|---|
| ***G01S 7/35*** | (2006.01) |
| *A61B 5/08* | (2006.01) |
| *A61B 5/11* | (2006.01) |
| *A61B 5/113* | (2006.01) |

(56) References Cited

U.S. PATENT DOCUMENTS

2015/0016824 A1* 1/2015 Roberts .............. H04B 10/1129 398/118
2020/0191945 A1* 6/2020 Leabman ................ G01S 7/282

OTHER PUBLICATIONS

Ghelfi et al., "Photonics in Radar Systems: RF Integration for State-of-the-Art Functionality", IEE Microwave Magazine, Sep. 2015, 16(8): 74-83.
International Search Report and Written Opinion of PCT International Patent Application No. PCT/AU2021/050396, mailed Jun. 25, 2021.
Ma et al., "Microwave Photonic Imaging Radar with a Millimeter-level Resolution", Journal of Lightwave Technology, Apr. 2020, 38(18): 4948-4954.
Canadian Application No. 3181380, Office Action dated Mar. 5, 2026, 6 pages.

* cited by examiner

RADAR SYSTEM HAVING A PHOTONICS-BASED SIGNAL GENERATOR

TECHNICAL FIELD

The present invention relates generally to radio detection and ranging (radar) systems and, in particular, to a radar system having a photonics-based signal generator.

BACKGROUND

Radio frequency (RF) and microwave radars have been widely used for civilian and military applications such as security inspection, internal non-destructive testing, autopilot assistance, and target identification. There are increasing demands for accurate ranging and high spatial resolution in these applications, which require radar systems to be operated at high microwave frequencies and broad bandwidth. However, designing a broadband radar is challenging due to the complexity in designing a wide bandwidth and high frequency electronic circuitry while still maintaining good signal quality.

Conventional electronic generation of wideband RF and microwave signals using direct digital synthesisers (DDSs) is limited to a few gigahertz. Further, multi-stage electronic mixers employed for frequency up-conversions degrade the signal-to-noise ratio of the generated radar signals. Also, the processing of wideband radar signals requires ultra-high-speed and expensive analog-to-digital (ADC) converters, of which signal processing precision degrades inversely with the signal bandwidth. There have been attempts to overcome such stringent limitations on microwave signal generation and processing by using optical devices and photonics-assisted technologies, which is referred to as microwave photonics.

One proposed photonics-assisted solution is to generate wideband RF and microwave radar signals using optical frequency quadrupling, which enlarges the input electric signals bandwidth by four times using an opto-electronic modulator that produces single-sideband modulated optical signals. However, this approach suffers from relying on expensive and bulky electronic digital arbitrary waveform generators (AWGs), which makes the radar system impractical for real-world applications. Moreover, the efficiency of signal generation is low due to the use of high-order modulated sidebands.

Another proposed technical solution is by employing fast sweeping lasers to generate frequency-modulated RF signals, which suffers from the low frequency linearity and high-cost of sweeping lasers, as the nonlinear frequency-to-time relationship significantly degrades the detection accuracy of radar systems.

SUMMARY

It is an object of the present invention to substantially overcome, or at least ameliorate, one or more disadvantages of existing arrangements.

The present disclosure describes a photonics-assisted frequency generator. The photonics-based frequency generator produces a stepped-frequency (SF) optical signal that is used for a radar system. Such a radar system is referred to as a photonics-based SF radar. The term SF hereinafter designates the temporal waveform of the generated optical signal, which manifests as a signal hopping by a fixed frequency step from the start frequency to the stop frequency, which is also referred to as 'chirped' signals.

According to an aspect of the present disclosure, there is provided a radar system comprising: a stepped-frequency optical signal generator configured for converting an optical signal into a stepped-frequency optical signal; an optical-to-electrical converter for converting the stepped-frequency optical signal into a stepped-frequency electrical signal; and a transmitter for transmitting a microwave signal based on the stepped-frequency electrical signal.

Other aspects are also disclosed.

BRIEF DESCRIPTION OF THE DRAWINGS

At least one embodiment of the present invention will now be described with reference to the drawings, in which.

DETAILED DESCRIPTION

It is to be noted that the discussions contained in the "Background" section and that above relating to prior art arrangements relate to discussions of documents or devices which form public knowledge through their respective publication and/or use. Such should not be interpreted as a representation by the present inventor(s) or the patent applicant that such documents or devices in any way form part of the common general knowledge in the art.

The radar system of the present disclosure uses a stepped-frequency microwave waveform to process a "received" or "reflected" radar signal in order to generate a "demodulated" microwave signal. The term "received" or "reflected" radar signal refers to the signal reflected from object(s) or target(s) to be detected or imaged which is (are) illuminated with the stepped-frequency microwave waveform generated by the radar system. The term "demodulated signal" refers to a received microwave signal that is sampled for extracting information regarding the object(s) or target(s).

Figure 1:
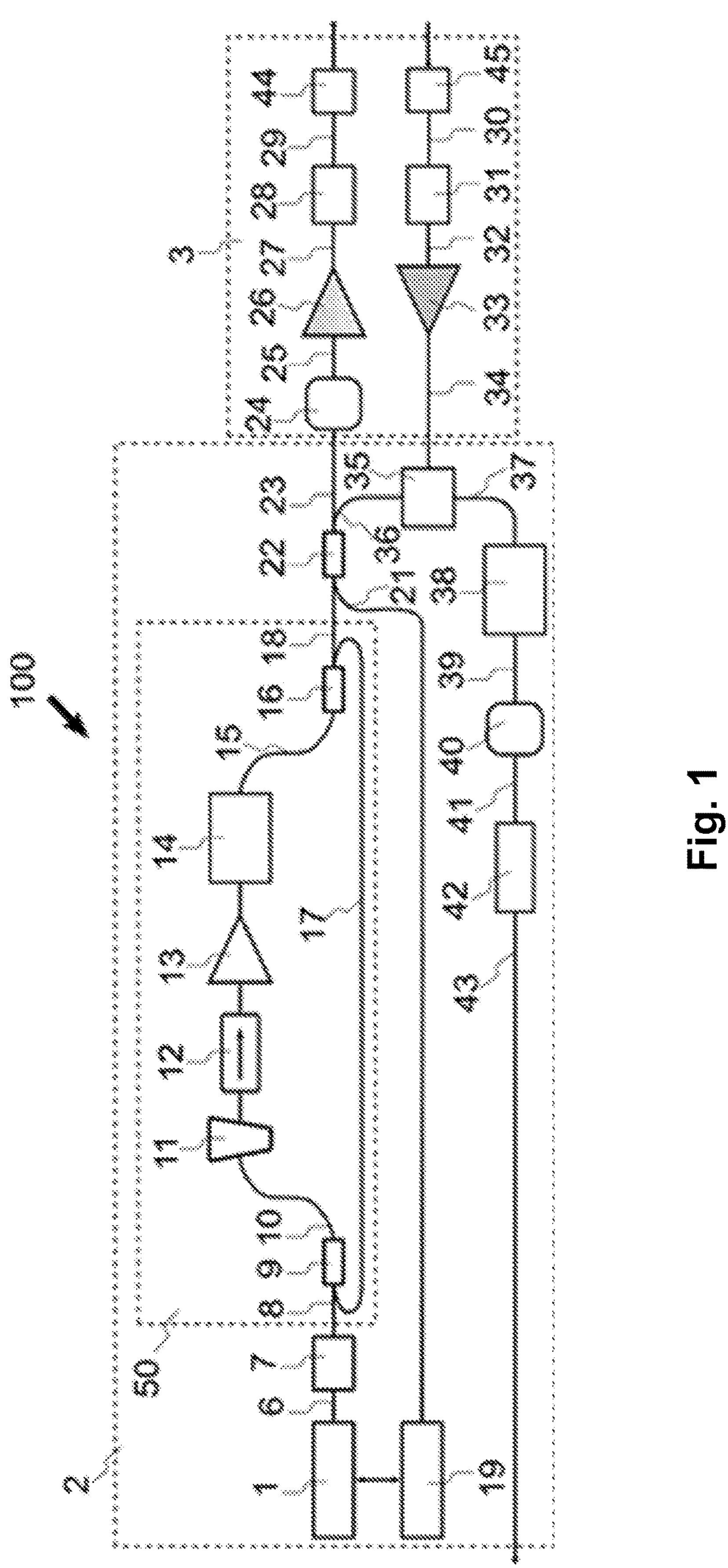
FIG. 1 depicts a block diagram of a photonics-based SF radar system in accordance with the present disclosure.

FIG. 1 shows a block diagram of a radar system 100 in accordance with the present disclosure. The radar system 100 includes an optical system 2 and an electrical system 3.

The optical system 2 is a fibre-based system for generating a SF optical signal that is then used to transmit a SF microwave radar signal and to process the SF microwave radar signal that has been reflected by objects. In alternative arrangements, the optical system 2 can be implemented using "free-space" system or "integrated-optics" system.

The electrical system 3 is configured to process the SF optical signal generated by the optical system 2 for transmitting a SF microwave radar signal and to provide the reflected SF microwave radar signal to the optical system 2.

In operation, the optical system 2 generates the SF optical signal at multiple frequencies, such that the SF optical signal hops between the different frequencies at different time instances. The electrical system 3 in turn converts the SF optical signal into a SF microwave radar signal, which is transmitted by the radar system 1. The electrical system 3 also receives the SF microwave radar signal that has been reflected by objects. The electrical system 3 then processes and provides the reflected SF microwave radar signal to the optical system 2. The optical system 2, in turn, processes the reflected signal to generate a demodulated signal.

Optical System 2

The optical system 2 has two separate parts: (1) a SF generator; and (2) a reflected signal processor.

The SF generator generates the SF optical signal. The SF generator includes a first light source 1, a second light source 19, an optical switch 7, an optical frequency shifting loop 50, and an X-junction optical beam splitting device 22. The SF generator produces the SF optical signal, which is used by the electrical system 3 and the reflected signal processor of the optical system 2.

The reflected signal processor processes the reflected signal in order to generate the demodulated signal, which in turn is used to obtain information regarding the object from which the signal is reflected. The reflected signal processor includes an electro-optic modulator 35, a tuneable optical bandpass filter 38, an optical-to-electrical converter 40, and an analog-to-digital converter 42.

SF Generator

In one arrangement, the light source 1 is a laser. The laser 1 is configured for transmitting an optical signal at a frequency $f_c$. In one arrangement, the frequency $f_c$ is in the terahertz region. The laser 1 has a narrow line width of around a few kHz or below and transmits the optical signal at a power of a few mW or above. The laser 1 transmits the optical signal to the optical switch 7.

In one arrangement, the light source 19 is a laser. The laser 19 is configured for transmitting an optical signal at a frequency $f_{LO}$. The laser 19 can be locked in phase with the laser 1 to reduce the phase noise of the generated radar signals. The optical signals from the lasers 1 and 19 have a frequency difference of $|f_c-f_{LO}|=f_0$. The frequencies of the lasers 1 and 19 are illustrated in FIG. 2.

Figure 2:
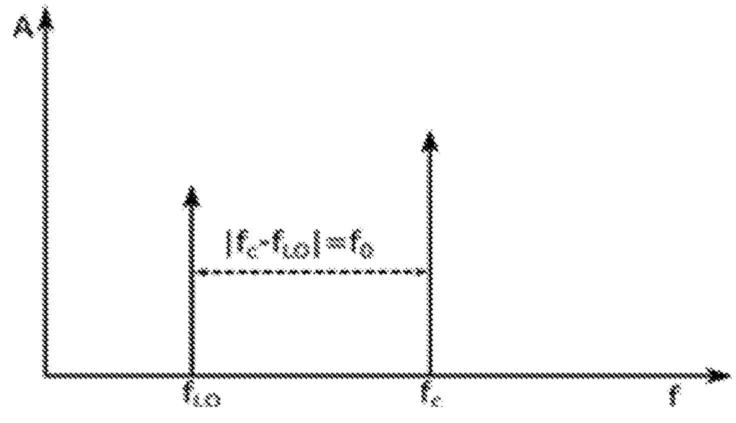
FIGS. 2 to 10 depict waveforms at different stages of the photonics-based SF radar system of FIG. 1.

FIG. 2 showing frequency $f_{LO}$ of the laser 19 to be lower than the frequency $f_c$ of the laser 1 is illustrative only. Frequency $f_{LO}$ of the laser 19 can be the same as or higher than the frequency $f_c$ of the laser 1.

In one alternative arrangement, the laser 19 is replaced by a device for single-sideband modulation. The single-sideband modulation device proportionally taps the output of the laser 1. The tapped output is then modulated by an electro-optic modulator that is driven by an oscillator at an RF frequency. The modulation provides a carrier-suppressed single-sideband modulated signal at the frequency $f_{LO}$, where the RF frequency applied by the oscillator to the electro-optic modulator provides the frequency shift from frequency $f_c$ of the laser 1 to the frequency $f_{LO}$.

The optical switch 7 converts the optical signal of laser 1 into an optical signal having one or more pulses. Each of the pulses has a pulse width $t_{sw}$. When there are multiple pulses, the pulses have a pulse repetition frequency $f_{sw}$ (i.e., two of the pulses are separated by a regular interval of time). The pulse width $t_{sw}$ and the pulse repetition frequency $f_{sw}$ are tuneable by controlling the parameters of the optical switch 7. In one arrangement, a processor is programmed and connected to the optical switch 7 to tune both the pulse width $t_{sw}$ and the pulse repetition frequency $f_{sw}$.

Figure 3:
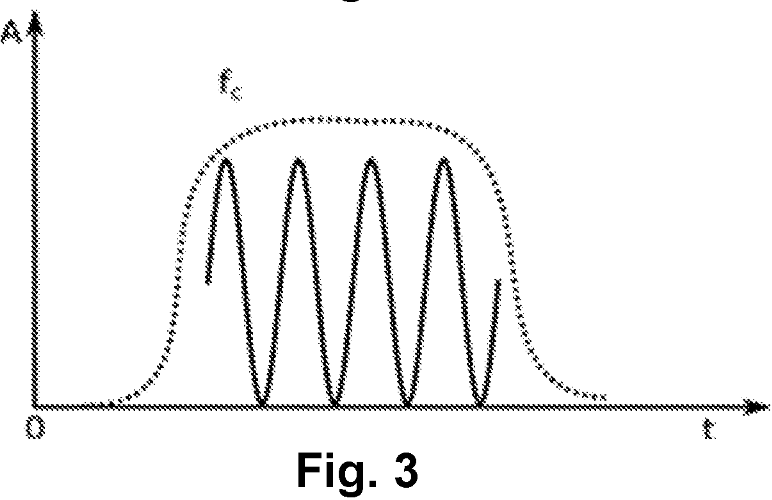

In one arrangement, the optical switch 7 is an optical modulator with an input 6 and an output 8. The input 6 receives the optical signal from the laser 1. The switch 7 then modulates the optical signal into a pulse-shaped optical signal (shown in FIG. 3). FIG. 3 shows only one of the pulses for simplicity sake.

The optical switch 7 generates the pulse-shaped optical signal by blocking and enabling transmission of the optical signal. The optical switch 7 blocks the transmission of the optical signal when the switch 7 is switched off. The optical switch 7 enables the transmission of the optical signal when the switch 7 is switched on. Therefore, by controlling the time that the switch 7 is switched on and off, the switch 7 controls the pulse width $t_{sw}$ and the pulse repetition frequency $f_{sw}$ of the generated pulse-shaped optical signal. When the optical switch 7 is switched on, the pulse-shaped optical signal at the output 8 is required to be higher by at least around 15 decibels in comparison to when the switch 7 is turned off, to generate the distinct pulses of the pulse-shaped optical signal at the output 8.

The pulse-shaped optical signal at the output 8 is then transmitted to the optical frequency shifting loop 50. The frequency shifting loop 50 processes the pulse-shaped optical signal into a SF optical signal.

The Frequency Shifting Loop 50 of the SF Generator

The optical frequency shifting loop 50 includes an optical beam splitting device 9, an optical frequency shifter 11, an optical isolator 12, an optical power amplifier 13, a tuneable optical bandpass filter 14, and an optical beam splitting device 16.

The optical beam splitting device 9 receives the pulse-shaped optical signal from the output 8 of the optical switch 7 and the stepped-frequency optical signal from an output 17 of the frequency shifting loop 50. The output 17 will be discussed further in relation to the optical beam splitting device 16 hereinafter. The optical beam splitting device 9 functions to add the pulse-shaped signal from the optical switch 7 into the frequency loop 50 and to recirculate the pulse-shaped signal from the output 17. The optical beam splitting device 9 then outputs the pulse-shaped signal at an output 10 to the optical frequency shifter 11. In one arrangement, the optical beam splitting device 9 is a 2-by-2 optical coupler with one of the outputs not in use.

The optical frequency shifter 11 shifts the frequency of the optical signal received from the optical beam splitting device 9. The frequency shift Δf can be up-conversion or down-conversion. The optical frequency shifter 11 is an acousto-optical shifter or modulator in which the frequency shift Δf occurs due to the light wave interacting with an acoustic wave travelling in a transparent solid. The frequency shift Δf can be from kilohertz to a few hundred megahertz. The frequency-shifted optical signal output of the optical frequency shifter 11 is then provided to the optical isolator 12.

The optical isolator 12 constrains the propagation of light in one direction, preventing the optical signal from propagating in the opposite direction. Accordingly, the optical isolator 12 may be placed at other locations within the frequency shifting loop 50 (e.g., between the optical beam splitting device 9 and the optical frequency shifter 11, between the optical power amplifier 13 and the tuneable optical bandpass filter 14, etc.). The light output of the optical isolator 12 is then provided to the optical power amplifier 13.

The optical power amplifier 13 amplifies the amplitude of the optical signal to compensate for energy losses that occur as the optical signal travels in the loop. The amplified optical signal is then provided to the tuneable optical bandpass filter 14.

The tuneable optical bandpass filter 14 enables light at a particular band to pass while blocking light at other bands. The bandwidth of the optical signal generated by the optical system 2 and the required bandwidth of the electrical system 3 are determined by the bandwidth of the filter 14. Bandwidth of the optical system 2 will be described in more detail hereinafter. In one arrangement, the filter 14 also suppresses the noise from the optical amplifier 13. An output 15 of the filter 14 is provided to the optical beam splitting device 16.

The optical beam splitting device 16 receives the optical signal from the filter 14 and splits the received optical signal at outputs 17 and 18. The output 17 is provided to the optical splitting beam device 9 (see above), while the output 18 is provided to the X-junction optical beam splitting device 22. The output 18 is the output of the optical frequency shifting loop 50, which is the stepped-frequency optical signal.

The operation of the SF generator is now described. The SF generator starts with the laser 1 generating the optical signal at a frequency $f_c$. The optical switch 7 receives the optical signal from the laser 1 via the input 6. The switch 7 converts the optical signal into a pulse-shaped optical signal having one or more pulses. As described above in relation to the switch 7, the pulses have a pulse repetition frequency $f_{sw}$ and each of the pulses has a pulse width $t_{sw}$. The pulse-shaped optical signal then enters the optical beam splitting device 9 of the optical frequency shifting loop 50.

Figure 5:
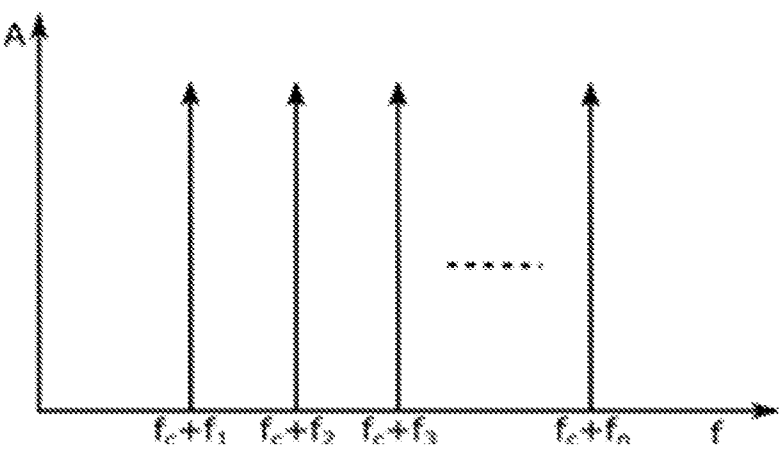

There are two cases to be considered for the optical frequency shifting loop 50. The first case relates to the pulse-shaped signal having only one pulse traveling in the loop. Each time the optical signal completes one travel in the loop 50, the frequency of the optical signal is shifted by a frequency shift $\Delta f$. As described above, the optical frequency shifter 11 causes the frequency shift $\Delta f$. When the single pulse signal travels n times in the loop 50, the frequency of the single pulse signal exiting the loop is $f_c+f_n$, where $f_n=n\times\Delta f$. FIG. 5 shows the spectrum of the single pulse signal as the single pulse signal travels n times in the loop 50.

Figure 4:
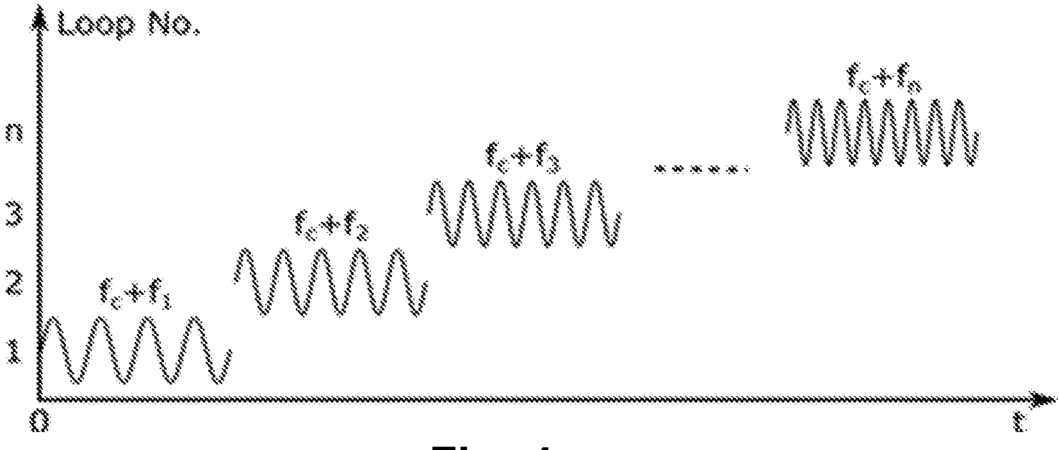

The optical switch 7 can be programmed so that the pulse width $t_{sw}$ equals to the loop travel time $t_{loop}$ (which is the time taken for the optical signal to undergo one travel of the loop 50). When the pulse width $t_{sw}$ equals to the loop travel time $t_{loop}$, the optical signal provided at the output 18 has no overlaps between two waveforms resulting from the frequency shift. FIG. 4 shows the optical waveforms corresponding to the number of the travels by the optical signal in the loop.

The total bandwidth of the SF optical signal output by the optical beam splitting device 16 is determined by the tuneable optical bandpass filter 14. Because the total bandwidth of the signal coupled out from the optical beam splitting device 16 equals to $n\times\Delta f$, the number of loop travel n is determined by the selected bandwidth of the filter 14.

The second case relates to the pulse-shaped optical signal having a plurality of pulses. Each single pulse acts in the same manner as described above in relation to the first case. However, for the second case, a pulse (which has been frequency shifted n times by the loop 50) may overlap with the next adjacent pulse. To prevent such an overlap, the pulse period, $T_{sw}=1/f_{sw}$, should equal to or larger than $(BW/\Delta f+1)\times t_{loop}$, where BW denotes the bandwidth of the optical bandpass filter 14.

Figure 6:
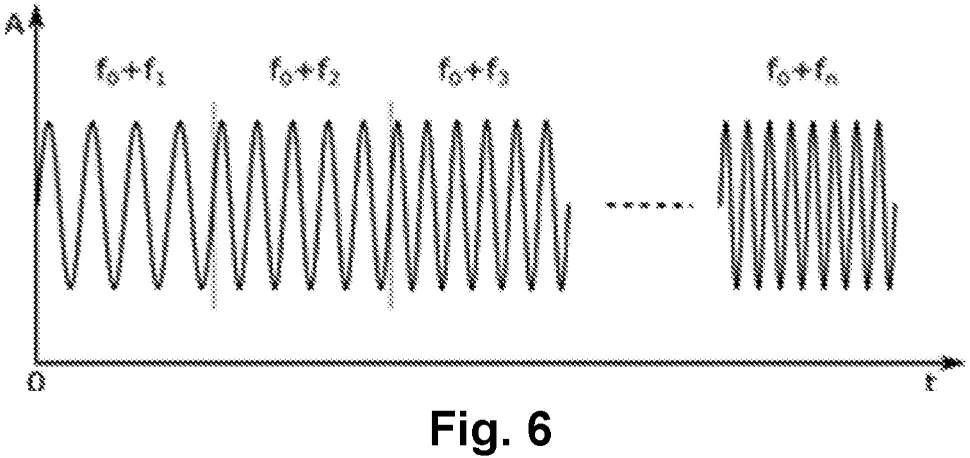

In both the first and second cases, the SF optical signal is generated in the optical domain with a frequency starting from $f_c$ and ending at $f_c+f_n$. The stepped-frequency optical signal has periodical pulses without any overlaps between two adjacent pulses by correctly adjusting the pulse repetition frequency $f_{sw}$ and the relationships between the pulse width $t_{sw}$ and the loop travel time $t_{loop}$. FIG. 6 depicts the SF optical signal output of the frequency shifting loop 50.

The SF optical signal output of the optical frequency shifting loop 50 is provided to the X-junction beam splitting device 22 after traveling n times in the loop 50. As described above, the output of the loop 50 is provided at the output 18 of the beam splitting device 16. The X-junction beam splitting device 22 also receives an optical signal from the laser 19 via input 21. Therefore, the X-junction optical beam splitting device 22 receives both the SF optical signal from the SF generator and the optical signal from the laser 19. The X-junction optical beam splitting device 22 then provides both optical signals at each of its outputs 23 and 36. The output 23 is provided to the electrical system 3, while the output 36 is provided to the reflected signal processor of the optical system 2.

The optical signal provided at the outputs 23 and 36 are referred to as a reference signal. The reference signal includes the optical stepped-frequency signal with a bandwidth from $f_c$ to $f_c+f_n$; and the optical signal from the laser 19 at a frequency $f_{LO}$. The reference signal therefore has a stepped-frequency signal with a bandwidth from $f_0$ to $f_0+f_n$, where $f_0=|f_c-f_{LO}|$. Accordingly, the combination of optical signal from the laser 19 and the optical signal from the laser 1 sets the carrier frequency of the radar system 100.

In one arrangement, each of the outputs 23 and 36 has a 50:50 ratio between the stepped-frequency optical signal from the loop 50 and the optical signal from the laser 19. In other arrangements, different ratios of the optical signals may be used.

The Reflected Signal Processor

As described above, the reflected signal processor includes the electro-optic modulator 35, the tuneable optical bandpass filter 38, the optical-to-electrical converter 40, and the analog-to-digital converter 42.

Figure 7:
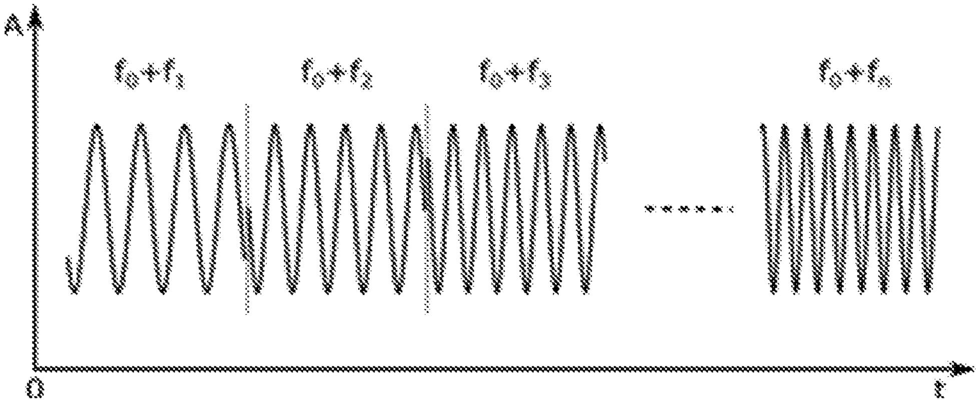
Figure 8:
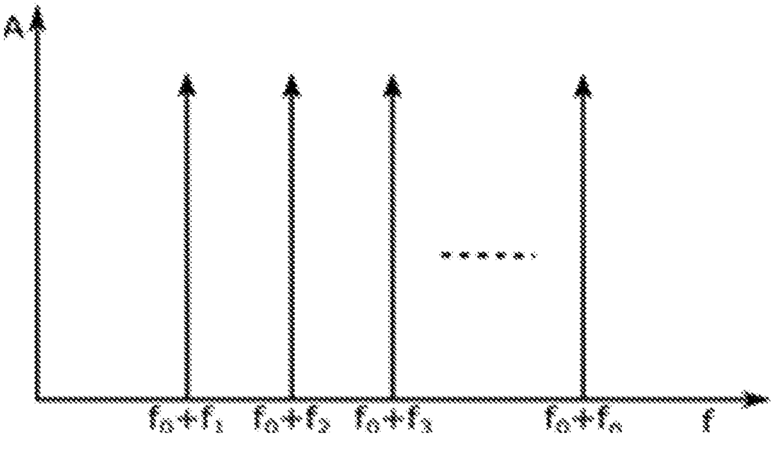

The electro-optic modulator 35 receives the reflected signal (from the electrical system 3) and the reference signal (from the X-junction beam splitting device 22 of the optical system 2). The reflected signal received by the electrical system 3 has a bandwidth from $f_0$ to $f_0+f_n$, similar to the SF optical signal. The reflected signal is shown in FIG. 7 in the time domain. FIG. 8 gives the spectrum of the reflected signal. However, there are phase differences between the SF optical signal (shown in FIG. 6) and the reflected signal (shown in FIG. 7), as the reflected signal has a time delay resulting from the distance travelled through the electrical system 3, free space, and reflected by the object. The reflected signal from the electrical system 3 modulates the reference signal from the X-junction beam splitting device 22 to generate a demodulated signal, which is effectively a combination of the SF optical signal and the reflected signal.

The electro-optic modulator 35 outputs the demodulated signal, which is at the frequency of $f_c$. The demodulated signal is provided at an output 37, which provides the demodulated signal to the tuneable optical bandpass filter 38.

The tuneable optical bandpass filter 38 has a bandpass in the range of $f_c$ to $f_c+f_n$. The filter 38 receives the demodulated signal of the electro-optic modulator 35 and filters the demodulated signal so that only the signal in the bandpass is output at an output 39. The filtering of the filter 38 selects the signal of interest and removes other irrelevant signals. The output signal of the filter 38 includes the optical SF signal with a bandwidth from $f_c$ to $f_c+f_n$; and the sideband of interest.

These two spectral components of the output signal of the filter 38 have the same bandwidth and frequency. However, the time domain signal of the sideband of interest has phase differences caused by the time delay due to the propagation of the reflected signal through the electrical system 3 and free space. The output signal of the filter 38 is provided at the output 39, which is then received by the optical-to-electrical converter 40.

Figure 9:
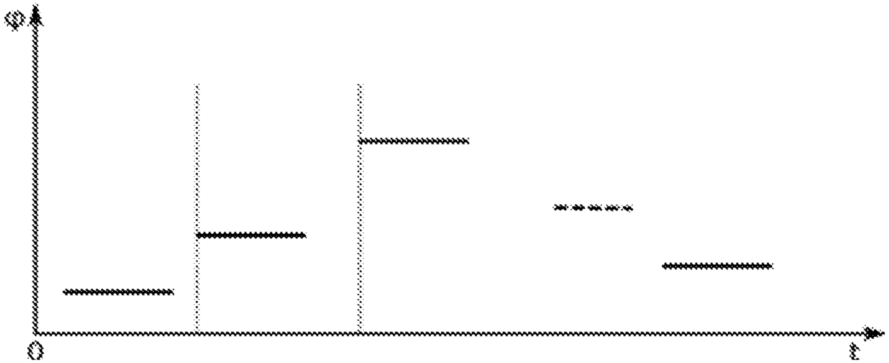

The optical-to-electrical converter 40 converts the output optical signal (i.e., the filtered demodulated signal) of the filter 38 into an electrical signal. FIG. 9 shows the phase differences of the reflected signal at the different frequencies of $f_c$ to $f_c+f_n$. The optical-to-electrical converter 40 only requires a passband that is lower than $f_n$, which may be in the kilohertz to megahertz range. In this frequency range, high-frequency interferences are filtered out by the RF bandwidth of the optical-to-electrical converter 40. The converter 40 then provides the electrical signal at an output 41. The output electrical signal is then sampled using the analog-to-digital converter 42. The sampled electrical signal can then be processed by a processor to extract information on an object from which the signal (which is transmitted by the transmitter 44) is reflected.

Figure 10:
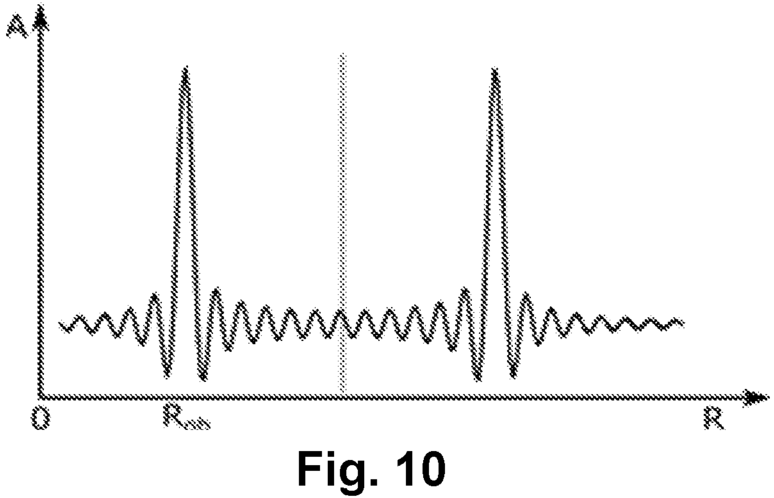

The phase differences of the reflected signal at the different frequencies of $f_c$ to $f_c+f_n$ can be expressed as:

$$\varphi(n) = \sum_{m=1}^{n} e^{-i2\pi m\Delta f\frac{2d}{c}},$$

where n is the number of travels, e is the Euler's number, i is the imaginary unit, Δf is the frequency shift, 2d is the round-trip distance between the radar system 100 and the targets, and c is the propagation speed of the signal emitted by the transmitter of the electrical system 3 (to be discussed below). Then, the time delay $$\frac{2d}{c}$$

can be extracted using signal processing methods (e.g., Fourier transform). FIG. 10 shows the result of range detection using the radar system 100 with a single target located at a distance $R_{ob}$. The result in FIG. 10 is periodic because the output signal of the analog-to-digital converter 42 is processed digitally.

The Electrical System 3

The electrical system 3 processes the stepped-frequency optical signal generated by the optical system 2. The electrical system 3 also receives the microwave radar signals reflected by objects and provides the reflected signals to the optical system 2.

As described above, the electrical system 3 receives the optical signals from the output 23 of the X-junction beam splitting device 22. The electrical system 3 includes a transmitter and a receiver. The transmitter is configured for converting the SF optical signal from the optical system 2 into microwave signals, which are transmitted as microwave radar signals. The receiver is configured for receiving the microwave radar signals reflected by objects.

Transmitter

The transmitter of the electrical system 3 includes an optical-to-electrical converter 24, an electronic amplifier 26, an electronic signal control unit 28, and a transmitting device 44.

The optical-to-electrical converter 24 converts the received optical signals (from the output 23 of the X-junction beam splitting device 22) into an electrical signal. The electrical signal at an output 25 of the optical-to-electrical converter 24 has the same pulse repetition frequency and duty cycle as the signal at the output 18 in the optical domain. The electrical signal at the output 25 has a bandwidth with the frequency ranging from $f_0$ to $f_0+f_n$. The bandwidth of the optical-to-electrical converter 24 is required to be equal to or larger than $f_0+f_n$. As described above in relation to the laser 19, $f_0=|f_c-f_{LO}|$.

The electrical SF waveform at the output 25 of the optical-to-electrical converter 24 is amplified by the electrical amplifier 26. The electrical amplifier 26 then provides the amplified electrical SF waveform at an output 27. In turn, the amplified electrical SF waveform is provided to the electronic signal control unit 28.

The electronic signal control unit 28 is an electronic circuit for processing (e.g., filtering, power limiting, and time-gating) the electrical SF waveform before providing the electrical SF waveform (via an output 29) to the transmitting device 44. The electronic signal control unit 28 is not described in detail for convenience sake.

The transmitting device 44 is an antenna or antennas for radiating electromagnetic signals. The transmitting device 44 receives the electrical SF signal from the electronic signal control unit 28 and radiates the SF signal accordingly.

Receiver

The SF signal being radiated by the transmitting device 44 reflects from objects. The receiver of the electrical system 3 then receives the reflected signals.

The receiver of the electrical system 3 includes a receiving device 45, an electronic signal control unit 31, and an electronic amplifier 34.

The receiving device 45 is an antenna or antennas for receiving electromagnetic signals (i.e., the reflected SF signal). The receiving device 45 then provides the reflected signals at an output 30. The output 30 is connected to the signal control unit 31.

The signal control unit 31 is an electronic circuit for processing (e.g., filtering, power limiting, and time-gating) the reflected signals from the receiving device 45. In some scenarios or applications, the time-gating function can be used to select signals reflected from a certain range to the device. The term "range" refers to the distance between the target and the radar system 100. The electronic signal control unit 31 is not described in detail for convenience sake. The signal control unit 31 then provides the processed signal at an output 32. The output 32 is connected to the electronic amplifier 33.

The electronic amplifier 33 amplifies the reflected signals and provides the amplified reflected signals at an output 34. The amplified reflected signals are then received by the electro-optic modulator 35 of the optical system 2. Refer to the description above on the reflected signal processor for processing the reflected signals.

Performance of the Radar System 100

Figure 12:
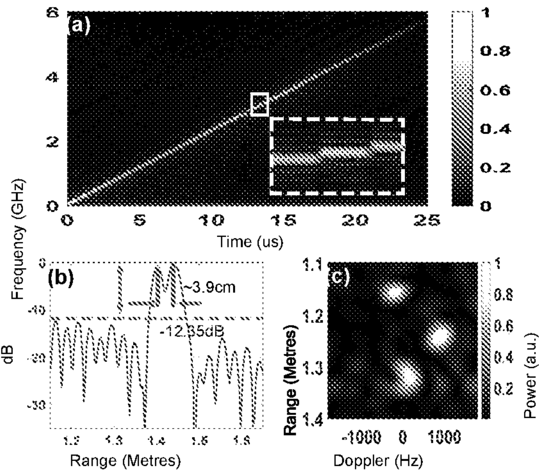
FIGS. 12(*a*) to 12(*c*) show performance results of the radar system of FIG. 1.
Figure 13:
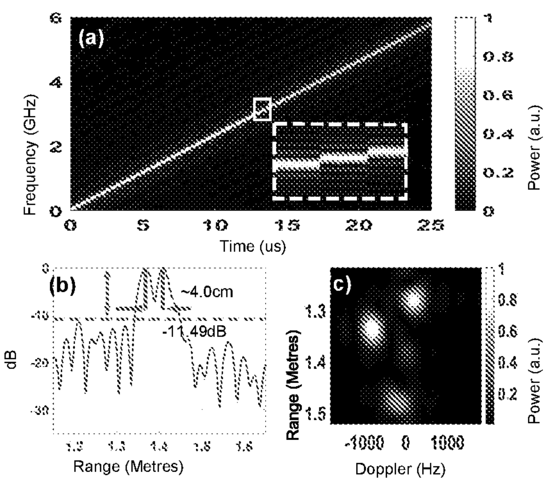
FIGS. 13(*a*) to 13(*c*) and 14(*a*) to 14(*c*) show performance results of the radar system of FIG. 11.
Figure 14:
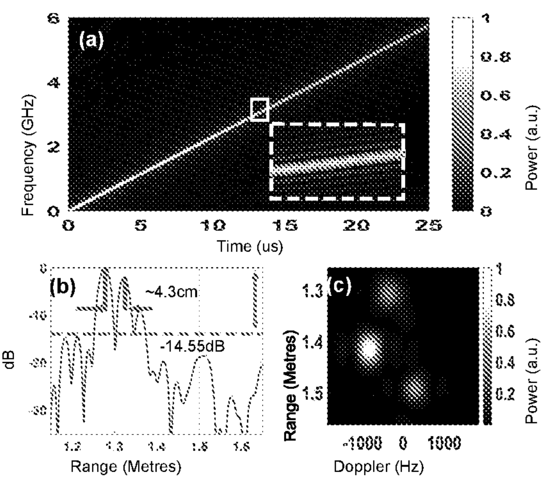

To demonstrate the performance and usability of the radar system 100, a comparison of the results of short-time Fourier transform (STFT), range detection, and imaging using the radar system 100 and the AWG-based radar system is shown in FIGS. 12 to 14.

Figure 11:
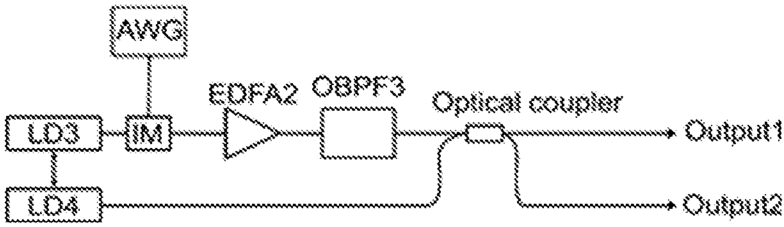
FIG. 11 shows a block diagram of an AWG radar system.

FIG. 11 shows an optical carrier of the AWG-based photonic signal generation system. The optical carrier is generated by a laser diode (LD3) and sent into an intensity modulator (IM) biased at the carrier suppression point. Baseband signals in the form of stepped frequency continuous wave (SFCW) or linear frequency modulated continuous wave (LFMCW) is generated by an AWG, which in this example uses Keysight, M8195A with 65 GSa/s. The baseband signals are sent into the IM with only one sideband selected by an optical bandpass filter (OBPF3). One output (Output1) of the system can be converted into electronic domain and processed by a radar front end to be transmitted. One example of the radar front end is the electrical system 3 of the radar system 100. Another output (Output2) can be used as a reference signal for coherent detection. One example of such optical-electronic coherent detection system from the radar system 100 is shown in FIG. 11.

FIG. 12(*a*) shows the STFT of the baseband signal generated by the optical system 2 of the radar system 100 and recorded by a real-time oscilloscope at a sampling rate of 40 GSa/s, which consists of ~72 steps forming a bandwidth of 5.76 GHz. With such a bandwidth, the radar system 100 has a theoretical range resolution of ~2.6 cm.

The AWG of FIG. 11 is set with the same number of steps (72 steps) and frequency-shift (80 MHz) per step to keep the bandwidth the same as that generated by the optical system 2. The STFT of the SFCW signal generated by the AWG is shown in FIG. 13(*a*). The transmitting power in each individual experiment is maintained to be approximately equal.

FIG. 14(*a*) shows the LFMCW signal of the AWG radar. The LFMCW signal is set to be the same bandwidth as the SFCW signal for comparison, as the same bandwidth sustains the same range resolution for the AWG radar using SFCW and LFMCW signals, respectively.

Two plane reflectors with a size of 1.5 cm×4 cm, placed at a distance of ~1.35 m with a space of 4 cm between the reflectors are used for range detections. The results are shown in FIG. 12(*b*), 13(*b*), and 14(*b*) with a measured spacing of 3.9 cm, 4.0 cm, and 4.3 cm, respectively. The errors among the range detections are introduced by the placement of the objects, and the resolution of the (inverse, in the case of SFCW) fast Fourier transform (FFT, 8192 points with an FFT resolution of ~0.25 cm) that is adopted for signal processing. The radar system 100 has a similar range resolution with a signal-to-noise ratio (SNR) of 12.35 dB, while the AWG-generated SFCW and LFMCW radar has an SNR of 11.49 dB and 14.55 dB, respectively. Therefore, the performance of the radar system 100 is similar to the performance of the AWG radar.

To demonstrate range-Doppler radar imaging, three cylindrical reflectors are mounted on a platform and rotated at a speed of ~35 rad/s, and the demodulated data from 90 reflected pulses are sampled for reconstructing an image. The imaging results based on the radar system 100, AWG-based SFCW, and AWG-based LFMCW, are presented in FIG. 12(*c*), 13(*c*), and 14(*c*), respectively. The results show that all the radar systems are able to reconstruct clear images, while the result from the radar system 100 has more speckle-like noise owing to the imperfectly chopped pulses with extended tails caused by inter-pulse crosstalk while recirculating. This drawback can be overcome using a high-performance optical switch to minimise the inter-pulse cross talk. The results also prove that the radar system 100 has good imaging performance compared with the other two commonly used AWG radars.

Example Application

One application of the radar system 100 is to detect the vital signs of human and animals. The vital signs include respiration rate, heart rate, and blood pressure.

The wide bandwidth tuning capabilities of the radar system 100 enables a resolution at the millimeter level. Such a resolution enables the radar system 100 to detect the chest displacements of human and animals. By extracting the chest displacement, the respiration frequency of the target(s) can be determined.

Figure 15:
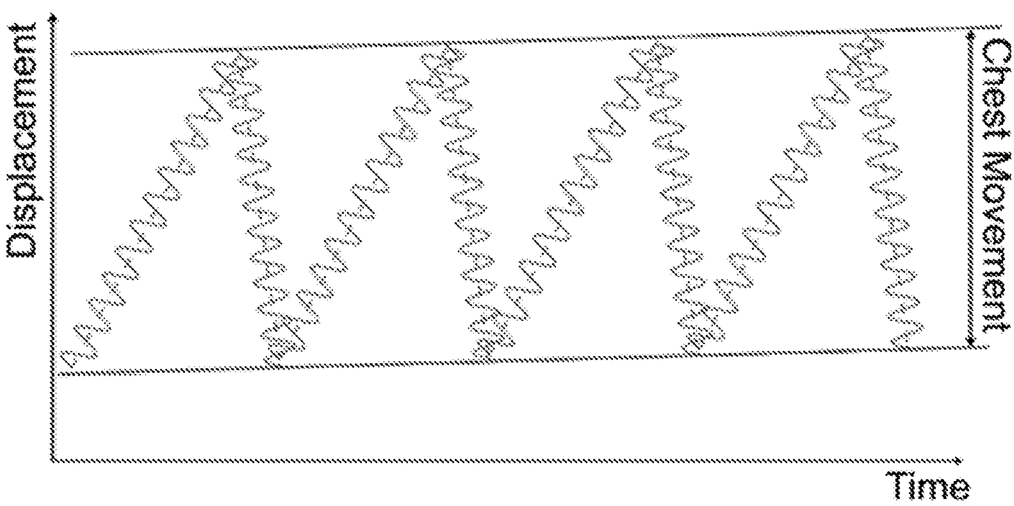
FIG. 15 shows a reflected radar signal of the radar system of FIG. 1 where the reflected radar signal is used to detect the respiration rate and heart rate of a target.

The wideband signal generated by the radar system 100 can be tuned to work at a different central frequency (wavelength) to enable the radar signal to penetrate regular human clothes and thin body tissues. Therefore, the reflected radar signal interacts with both chest movement and cardiac contraction. FIG. 15 shows a reflected radar signal that has been reflected from a target. For a human, the cardiac contraction has a frequency higher than the frequency of the chest movement. Therefore, these two frequencies (respiration rate and heart rate) can be separated on the frequency domain by digitally processing the received reflected signal from the radar system 100. The heart contractions modulate the respiration displacement with smaller amplitudes or fluctuations, as shown in FIG. 15. By applying Fourier transform to the reflected radar signal, the frequencies of the reflected signals can be determined, such that the lower frequency indicates the respiration rate of the target while the higher frequency indicates the cardiac contraction of the target.

Blood pressure is related to the heart rate and heart contractility (more specifically, stroke volume). With the information acquired by the radar system 100, signal processing methods and calibrations can be used to estimate the blood pressure of the target(s).

In an experiment, the radar system 100 is tuned to work at a bandwidth of 12 GHz corresponding to a range resolution of approximately 1.25 centimetres (cm). Two 2 by 6 centimetres thin aluminium plate mounted onto two programmable moving platforms separately are chosen as the targets to emulate human respiration. These two targets are programmed to move with displacements and frequency within the range of the respiration of an average human. It is noted that respiration rate would increase with fever, illness, and other medical conditions. Therefore, a determined respiration rate may determine that a target may possibly be ill.

Figure 16:
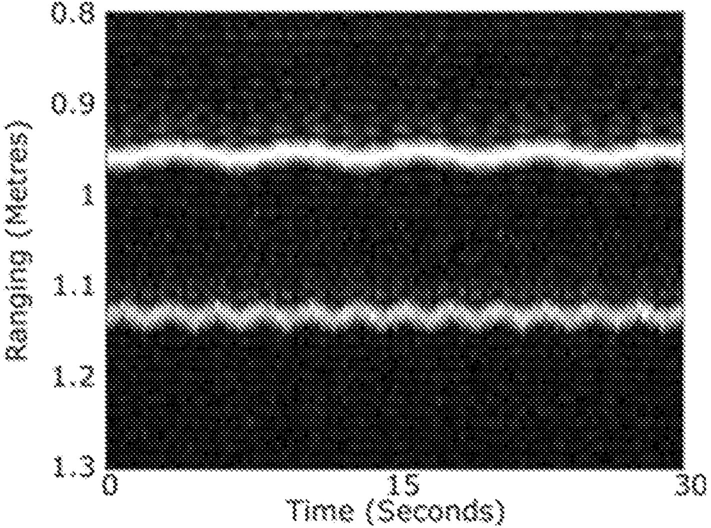
FIG. 16 show reflected radar signals of the radar system of FIG. 1 for detecting the respiration rates and heart rates of multiple targets.

FIG. 16 shows the detection of the respiration rates of two targets at different distances. Target one is located between 1.1 to 1.2 meters away from the radar system 100, and target two is located between 0.9 and 1 meters away from the radar system 100.

Figure 17:
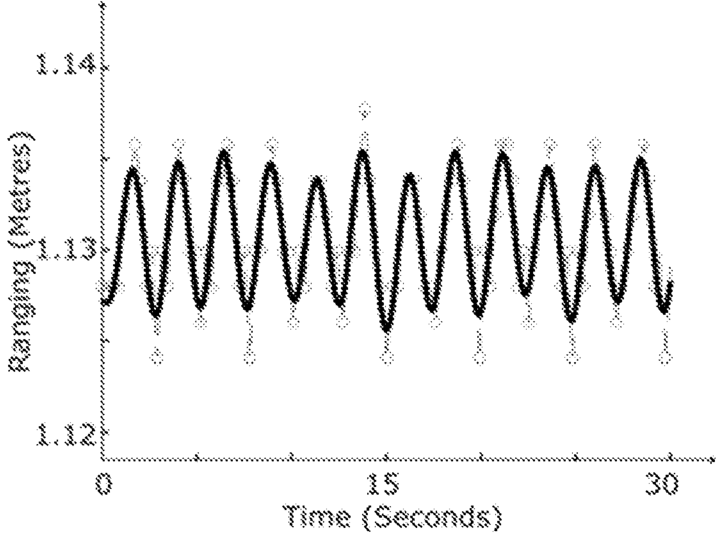
FIG. 17 is an enlarged plot of one of the targets in FIG. 16.
Figure 18:
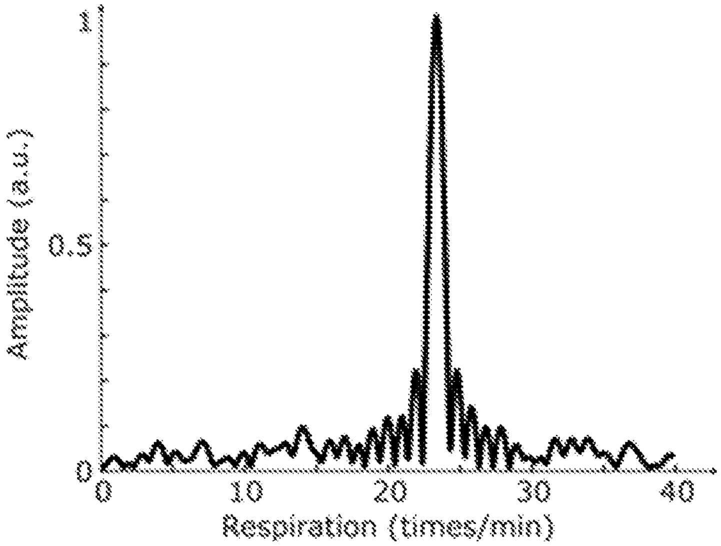
FIG. 18 shows the respiration rate of the target shown in FIG. 17.
Figure 19:
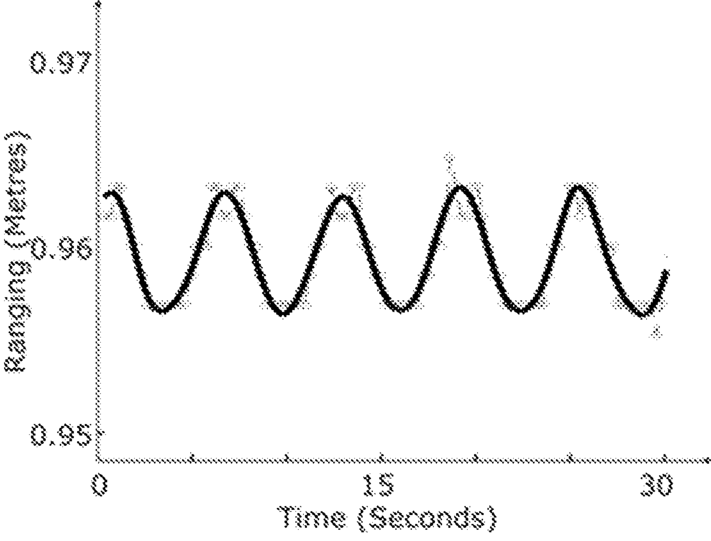
FIG. 19 is an enlarged plot of the other target in FIG. 16.
Figure 20:
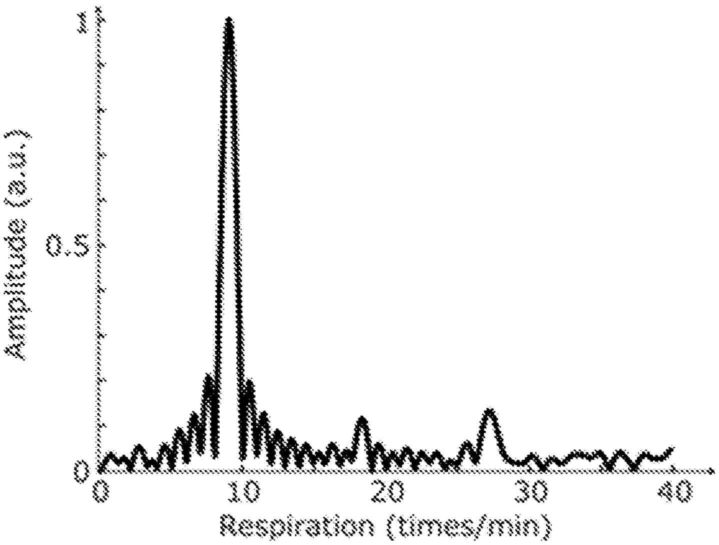
FIG. 20 shows the respiration rate of the target shown in FIG. 19.

FIG. 17 is the enlarged plot of the respiration rate measurement of target one. FIG. 18 shows that the respiration rate of target one is approximately 24 times per minutes. FIG. 19 is the enlarged plot of the respiration measurement of target two. FIG. 20 shows that the respiration rate of target two is approximately 9 times per minutes.

INDUSTRIAL APPLICABILITY

The arrangements described are applicable to the radar industries. The radar system 100 can be used with existing radar and detection technologies. Examples of such radar technologies are synthetic aperture radar imaging; ground penetrating radar; a multiple-input and multiple-output radar; and the like.

The radar system 100 can also acquire range and doppler information through the detection of multiple SF signals.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A radar system comprising:

a stepped-frequency optical signal generator configured for converting a first optical signal into a stepped-frequency optical signal;

a second light source configured for transmitting a second optical signal;

an X-junction optical beam splitting device configured for receiving the stepped-frequency optical signal and the second optical signal and for combining the received signals into a reference signal;

an optical-to-electrical converter for converting the reference signal into a stepped-frequency electrical signal; and a transmitter for transmitting a microwave signal based on the stepped-frequency electrical signal.

2. The radar system of claim 1, wherein the stepped-frequency optical signal generator comprises:

an optical switch for modulating the first optical signal into a pulse-shaped optical signal, the pulse-shaped optical signal having a pulse; and an optical frequency shifting loop for converting the pulse-shaped optical signal into the stepped-frequency optical signal.

3. The radar system of claim 2, wherein the optical frequency shifting loop comprises a frequency shifter to shift a frequency of the pulse.

4. The radar system of claim 2, wherein the pulse-shaped optical signal iteratively travels through the optical frequency shifting loop, wherein each iteration through the optical frequency shifting loop shifts the frequency of the pulse by a frequency shift.

5. The radar system of claim 1, further comprising a first light source for generating the first optical signal.

6. The radar system of claim 1, further comprising:

a receiver for receiving the transmitted microwave signal that is reflected by an object;

an electro-optic modulator for modulating the stepped-frequency optical signal with the received microwave signal to generate a demodulated optical signal; and an optical-to-electrical converter for converting the demodulated optical signal into an electrical signal, wherein the electrical signal is used to extract information regarding the object.

7. The radar system of claim 6, further comprising:

a filter for filtering the demodulated optical signal.

8. The radar system of claim 6, wherein the second optical signal in combination with the first optical signal modify a carrier frequency of the radar system.

9. The radar system of claim 1, wherein the radar system detects vital signs of a target, wherein the vital signals comprise respiration rate, heart rate, and blood pressure.

10. The radar system of claim 3, wherein the pulse-shaped optical signal iteratively travels through the optical frequency shifting loop, wherein each iteration through the optical frequency shifting loop shifts the frequency of the pulse by a frequency shift.

11. The radar system of claim 2, further comprising a first light source for generating the first optical signal.

12. The radar system of claim 3, further comprising a first light source for generating the first optical signal.

13. The radar system of claim 4, further comprising a first light source for generating the first optical signal.

14. The radar system of claim 2, further comprising:

a receiver for receiving the transmitted microwave signal that is reflected by an object;

an electro-optic modulator for modulating the reference signal with the received microwave signal to generate a demodulated optical signal; and an optical-to-electrical converter for converting the demodulated optical signal into an electrical signal, wherein the electrical signal is used to extract information regarding the object.

15. The radar system of claim 3, further comprising:

a receiver for receiving the transmitted microwave signal that is reflected by an object;

an electro-optic modulator for modulating the reference signal with the received microwave signal to generate a demodulated optical signal; and an optical-to-electrical converter for converting the demodulated optical signal into an electrical signal, wherein the electrical signal is used to extract information regarding the object.

16. The radar system of claim 4, further comprising:

a receiver for receiving the transmitted microwave signal that is reflected by an object;

an electro-optic modulator for modulating the reference signal with the received microwave signal to generate a demodulated optical signal; and an optical-to-electrical converter for converting the demodulated optical signal into an electrical signal, wherein the electrical signal is used to extract information regarding the object.

17. The radar system of claim 5, further comprising:

a receiver for receiving the transmitted microwave signal that is reflected by an object;

an electro-optic modulator for modulating the reference signal with the received microwave signal to generate a demodulated optical signal; and an optical-to-electrical converter for converting the demodulated optical signal into an electrical signal, wherein the electrical signal is used to extract information regarding the object.

18. The radar system of claim 7, wherein the second optical signal in combination with the first optical signal modify a carrier frequency of the radar system.

* * * * *